(12) United States Patent
Tempelman et al.

(10) Patent No.: US 10,091,985 B2
(45) Date of Patent: Oct. 9, 2018

(54) PERFUSING AN ORGAN WITH AN IN SITU GENERATED GAS

(75) Inventors: Linda A. Tempelman, Lincoln, MA (US); Klearchos K. Papas, Maple Grove, MN (US); Simon G. Stone, Arlington, MA (US); William Earl Scott, III, Saint Paul, MN (US); Thomas M. Suszynski, Maple Plain, MN (US); Shuichiro Matsumoto, Uwajima Ehime (JP); Joana Ferrer Fabrega, Girona (ES); Michael D. Rizzari, Saint Paul, MN (US)

(73) Assignee: GINER, INC., Newton, MA (US)

( * ) Notice: Subject to any disclaimer, the term of this patent is extended or adjusted under 35 U.S.C. 154(b) by 259 days.

(21) Appl. No.: 12/803,083

(22) Filed: Jun. 18, 2010

(65) Prior Publication Data

US 2010/0330547 A1   Dec. 30, 2010

Related U.S. Application Data

(60) Provisional application No. 61/268,973, filed on Jun. 18, 2009.

(51) Int. Cl.
*A01N 1/02* (2006.01)

(52) U.S. Cl.
CPC ......... *A01N 1/0247* (2013.01); *A01N 1/0226* (2013.01)

(58) Field of Classification Search
CPC ..... A01N 1/0247; A01N 1/0226; A01N 1/021
See application file for complete search history.

(56) References Cited

U.S. PATENT DOCUMENTS

| 4,057,479 A | 11/1977 | Campbell |
| 5,011,472 A | 4/1991 | Aebischer et al. |

(Continued)

FOREIGN PATENT DOCUMENTS

| CA | 2112952 A1 | 6/1995 |
| CN | 1036511 A | 10/1989 |

(Continued)

OTHER PUBLICATIONS

Burns et al., The Survival of Mammalian Tissues Perfused with Intravascular Gas Mixtures of Oxygen and Carbon Dioxide, Canadian Journal of Biochemistry and Phiysiology, 1958, vol. 36, pp. 499-504.*

(Continued)

*Primary Examiner* — Kara D Johnson
(74) *Attorney, Agent, or Firm* — Kriegsman & Kriegsman

(57) ABSTRACT

Method and system for organ preservation. According to one aspect, an organ may be preserved by being perfused with an in situ generated preserving gas. The organ may be, for example, a human or porcine pancreas, and perfusion of the pancreas may be anterograde, retrograde, ductal, anterograde/ductal, or retrograde/ductal. The preserving gas used to perfuse the organ may be dissolved in a liquid and then administered to the organ as a gas/liquid solution or may be mixed with one or more other gases and then administered to the organ as a gas/gas mixture. The preserving gas may be, for example, oxygen gas generated in situ using an electrochemical oxygen concentrator. According to another aspect, an organ preservation system may include an electrochemical oxygen concentrator having a water vapor feed, as well as auxiliary equipment to control and measure delivery pressure, flow, temperature and humidity.

51 Claims, 9 Drawing Sheets

(56) References Cited

U.S. PATENT DOCUMENTS

| | | | |
|---|---|---|---|
| 5,338,662 A * | 8/1994 | Sadri | 435/284.1 |
| 5,356,771 A * | 10/1994 | O'Dell | 435/284.1 |
| 5,362,622 A | 11/1994 | O'Dell et al. | |
| 5,385,821 A | 1/1995 | O'Dell et al. | |
| 5,586,438 A | 12/1996 | Fahy | |
| 5,788,682 A | 8/1998 | Maget | |
| 5,951,538 A | 9/1999 | Joshi et al. | |
| 5,965,433 A | 10/1999 | Gardetto et al. | |
| 6,060,640 A | 5/2000 | Pauley et al. | |
| D453,828 S | 2/2002 | Brassil et al. | |
| 6,368,592 B1 | 4/2002 | Colton et al. | |
| 6,475,716 B1 * | 11/2002 | Seki | 435/1.3 |
| 6,492,103 B1 | 12/2002 | Taylor | |
| 6,673,594 B1 | 1/2004 | Owen et al. | |
| 6,677,150 B2 | 1/2004 | Alford et al. | |
| 6,773,458 B1 | 8/2004 | Brauker et al. | |
| 6,977,140 B1 | 12/2005 | Owen et al. | |
| 6,994,954 B2 | 2/2006 | Taylor | |
| 7,176,015 B2 | 2/2007 | Alford et al. | |
| 7,572,622 B2 | 8/2009 | Hassanein et al. | |
| 7,651,835 B2 | 1/2010 | Hassanein et al. | |
| 7,892,222 B2 | 2/2011 | Vardi et al. | |
| 7,947,094 B2 | 5/2011 | Fiebig | |
| 8,012,500 B2 | 9/2011 | Rotem et al. | |
| 8,043,271 B2 | 10/2011 | Stern et al. | |
| 8,083,821 B2 | 12/2011 | Tempelman et al. | |
| 9,357,764 B2 | 6/2016 | Tempelman et al. | |
| 2002/0033333 A1* | 3/2002 | Riecke | 204/256 |
| 2003/0087427 A1* | 5/2003 | Colton et al. | 435/289.1 |
| 2004/0058432 A1 | 3/2004 | Owen et al. | |
| 2005/0221269 A1* | 10/2005 | Taylor et al. | 435/1.1 |
| 2006/0160204 A1 | 7/2006 | Hassanein et al. | |
| 2006/0292544 A1 | 12/2006 | Hassanein et al. | |
| 2008/0187901 A1 | 8/2008 | Doorschodt et al. | |
| 2008/0226750 A1 | 9/2008 | Roth et al. | |
| 2008/0248350 A1 | 10/2008 | Little et al. | |
| 2009/0012502 A1 | 1/2009 | Rotem et al. | |
| 2009/0112170 A1 | 4/2009 | Wells et al. | |
| 2009/0197240 A1 | 8/2009 | Fishman et al. | |
| 2010/0196439 A1 | 8/2010 | Beck et al. | |
| 2010/0204683 A1 | 8/2010 | Bodor et al. | |
| 2011/0054387 A1 | 3/2011 | Stern et al. | |
| 2011/0212431 A1 | 9/2011 | Bunegin et al. | |
| 2011/0295241 A1 | 12/2011 | Ziaie et al. | |
| 2012/0178150 A1 | 7/2012 | Tempelman et al. | |
| 2015/0112247 A1 | 4/2015 | Tempelman et al. | |

FOREIGN PATENT DOCUMENTS

| | | |
|---|---|---|
| CN | 101569559 A | 11/2009 |
| JP | 1995196401 A | 8/1995 |
| JP | 2008519830 A | 6/2008 |
| WO | 0150983 A1 | 7/2001 |
| WO | 2006112720 A2 | 10/2006 |
| WO | 2006122169 A2 | 11/2006 |
| WO | 2008079997 A2 | 7/2008 |
| WO | 2009031154 A2 | 3/2009 |
| WO | 2010049996 A1 | 5/2010 |

OTHER PUBLICATIONS

Hunt et al., Cannulation of the portal vein for cytotoxic liver perfusion in colorectal carcinomas: an alternative approach, Annals of the Royal College of Surgeons of England, 1986, vol. 68, pp. 36-38.*

Sudan et al., A New Technique for Combined Liver/Small Intestine Transplantation, Transplantation, 2001, vol. 72, pp. 1846-1848.*

Kuhn-Regnier et al., Coronary oxygen persufflation combined with HTK carioplegia prolongs the preservation time in heart transplantation, European Journal of Cardio-thoracic Surgery, 2000, vol. 17, pp. 71-76.*

Kin et al., Islet Isolation and Transplantation Outcomes of Pancreas Preserved with University of Wisconsin Solution Versus Two-Layer Method Using Preoxygenated Perfluorocarbon, Transplantation • vol. 82, No. 10, Nov. 27, 2006, pp. 1286-1290.*

Ohsawa, et al., Hydrogen acts as a therapeutic antioxidant by selectively reducing cytotoxic oxygen radicals, Nature Medicine, 2007, vol. 13, pp. 688-694.*

Saad et al., Extension of Ischemic Tolerance of Porcine Livers by Cold Preservation Including Postconditioning With Gaseous Oxygen, Transplantation, 2001, vol. 71, pp. 498-502.*

Suszynski et al., "Persufflation (or gaseous oxygen perfusion) as a method of organ preservation," Cryobiology, 64(3):125-43 (2012).

Kuhn-Regnier et al., "Coronary oxygen persufflation combined with HTK cardioplegia prolongs the preservation time in heart transplantation," European Journal of Cardio-thoracic Surgery, 17:71-6 (2000).

Fischer, "Methods of Cardiac Oxygen Persufflation," Methods in Bioengineering: Organ Preservation and Reengineering, editors Korkut Uygun and Charles Y. Lee, published by Artech House, Norwood, MA (2011).

Treckmann et al., "Retrograde Oxygen Persufflation Preservation of Human Livers: A Pilot Study," Liver Transplantation, 14:358-64 (2008).

Wood et al., "The hydrogen highway to reperfusion therapy," Nature Medicine, 13(6):673-4 (2007).

Ohsawa et al., "Hydrogen acts as a therapeutic antioxidant by selectively reducing cytotoxic oxygen radicals, Nature Medicine," 13(6):688-94 (2007).

Koetting et al., "Optimal Time for Hypothermic Reconditioning of Liver Grafts by Venous Systemic Oxygen Persufflation in a Large Animal Model," Transplantation, 91(1):42-7 (2011).

Guibert et al., "Organ Preservation: Current Concepts and New Strategies for the Next Decade," Transfusion Medicine and Hemotherapy, 38:125-42 (2011).

Caballero-Corbalan et al., "No Beneficial Effect of Two-Layer Storage Compared With UW-Storage on Human Islet Isolation and Transplantation," Transplantation, 84(7):864-9 (2007).

Minor et al., "Energetic recovery in porcine grafts by minimally invasive liver oxygenation," Journal of Surgical Research, published online Mar. 14, 2012.

Moers et al., "Machine Perfusion or Cold Storage in Deceased-Donor Kidney Transplantation," N. Eng. J. Med., 360:7-19 (2009).

Emamaullee et al., "Caspase Inhibitor Therapy Synergizes With Costimulation Blockade to Promote Indefinite Islet Allograft Survival," Diabetes, 59:1469-77 (2010).

Emamaullee et al., "The Caspase Selective Inhibitor EP1013 Augments Human Islet Graft Function and Longevity in Marginal Mass Islet Transplantation in Mice," Diabetes, 57:1556-66 (2008).

Expanding Transplantation Possibilities, Lifeline Scientific Annual Report 2010, Lifeline Scientific, Inc., Itasca, Illinois.

Calhoon et al., "Twelve-Hour Canine Heart Preservation With a Simple, Portable Hypothermic Organ Perfusion Device," Ann. Thorac. Surg., 62:91-3 (1996).

Hassanein et al., "Continuous Perfusion of Donor Hearts in the Beating State Extends Preservation Time and Improves Recovery of Function," J. Thorac. Cardiovasc. Surg., 116:821-30 (1998).

Weegman et al., "Continuous Real-time Viability Assessment of Kidneys Based on Oxygen Consumption," Transplant Proc., 42(6):200-23 (2010).

English translation of Office Action dated Jul. 8, 2014, in Japanese Patent Application No. 2012-284992, said application being the counterpart Japanese patent application to U.S. Appl. No. 13/341,565, which is a continuation-in-part to the present application.

Blakemore et al., "Molecular Catalysts for Water Oxidation," Chem. Rev., 115:12974-13005 (2015).

Scott et al., "Persufflation Improves Pancreas Preservation When Compared With the Two-Layer Method," Transplantation Proceedings, 42(6):2016-2019 (Jul.-Aug. 2010).

Scott et al., "Pancreas Oxygen Persufflation Increases ATP Levels as Shown by Nuclear Magnetic Resonance," Transplantation Proceedings, 42(6): 2011-2015 (Jul.-Aug. 2010).

Weegman et al., "Continuous Real-Time Viability Assessment of Kidneys Based on Oxygen Consumption," Transplant Proc., 42(6): 2020-2023 (2010).doi:10.1016/j.transproceed.2010.05.082.

(56) References Cited

OTHER PUBLICATIONS

Tibell et al., "Survival of Macroencapsulated Allogenic Parathyroid Tissue One Year After Transplantation in Nonimmunosuppressed Humans," Cell Transplantation, 10:591-599 (2001).
Wu et al., "In Situ Electrochemical Oxygen Generation with an Immunoisolation Device," Ann. N.Y. Acad. Sci., pp. 105-125 (1999).
J.H. Fischer: Methods of Cardiac Oxygen Persufflation. Author manuscript available at ResearchGate.net Mar. 15, 2018. Published in final edited form as: Methods of Bioengineering: Organ preservation and reengineering. Eds. Korkut Uygun and Charles Y. Lee. Artech House Boston, London 2011, p. 105-126. ISBN: 13: 978-1-60807-013-8.
Taylor et al., "Current state of hypothermic machine perfusion preservation of organs: The clinical perspective," Cryobiology (2009), doi:10.1016/j.cryobiol.2009.10.006.
Avgoustiniatos et al., "Effect of External Oxygen Mass Transfer Resistances on Viability of Immunoisolated Tissue," Ann NY Acad Sci, 831:145-167 (1997).

* cited by examiner

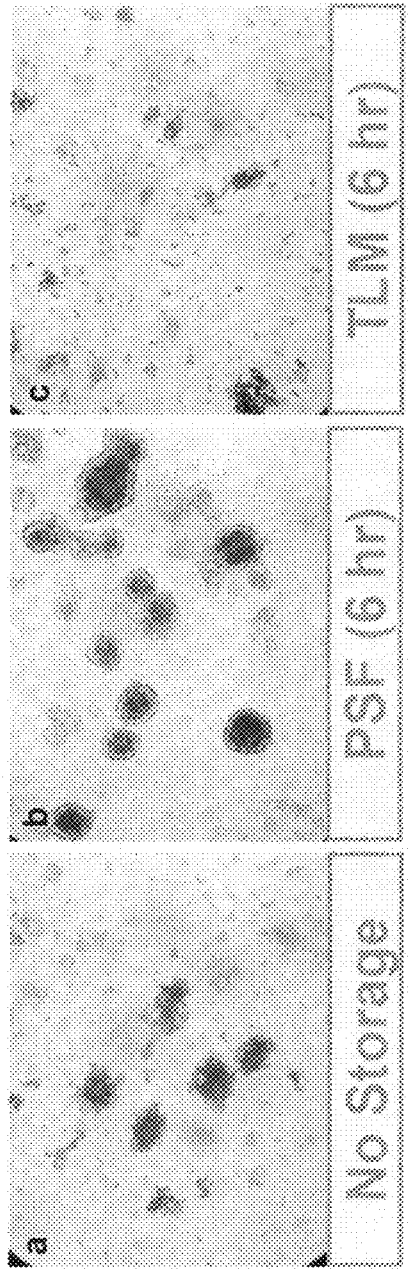

FIG. 5(a)  No Storage
FIG. 5(b)  PSF (6 hr)
FIG. 5(c)  TLM (6 hr)

Comparison of preservation methods based on islet yield and quality.

| Preservation Method | Pancreas Lobe | n | Day 0 IE Yield IE/g | Day 2 IE Recovery % | Day 2 OCR/DNA nmol/(min·mg) | Day 2 OCR Yield nmol/(min·g) | Day 2 Fragmentation (DNA IE)/IE | Day 2 IE-Based OCR Yield nmol/(min·g) |
|---|---|---|---|---|---|---|---|---|
| None (0 hr) | Duodenal | 3 | 1395 ± 201[#] | 48 ± 13[#] | 185 ± 39 | 1.30 ± 0.36[#] | 1.00 ± 0.15 | 1.33 ± 0.11[#] |
| PSF (6 hr) | Splenic | 4 | 1430 ± 719 | 67 ± 30 | 199 ± 26 | 1.67 ± 0.54 | 1.38 ± 1.34 | 2.15 ± 1.43 |
| TLM (6 hr) | Connecting | 4 | 1298 ± 617 | 53 ± 40 | 173 ± 20 | 1.94 ± 1.20 | 3.70 ± 4.55 | 1.42 ± 1.04 |
| None (0 hr) | Duodenal | 1 | 1313 | 27 | 159 | 1.22 | 2.11 | 0.58 |
| PSF (24 hr) | Splenic | 1 | 1551 | 23 | 179 | 0.93 | 1.41 | 0.66 |
| TLM (24 hr) | Connecting | 1 | 1405 | 7 | 156[*] | 0.36[†] | 2.42 | 0.15[†] |

[*] n=2 due to a technical problem with the media that resulted in loss of isolated islets on day 0. [†] Calculated using day 1 OCR/DNA value. [#] Day 1 value due to lack of sufficient tissue to run OCR assay on day 2.

FIG. 6

Comparison of preservation methods based on the nude mouse bioassay (diabetes reversal rate, time to cure, and mean blood glucose concentration for nude mice transplanted with 2000 cultured porcine IE).

| Preservation Culture Time | Immediate Isolation | | 6-hour PSF | | 24-hour PSF | | 6-hour TLM | | 24-hour TLM | |
|---|---|---|---|---|---|---|---|---|---|---|
| Pig Number | 2 d | 7 d | 2 d | 7 d | 2 d | 7 d | 2 d | 7 d | 2 d | 7 d |
| P647 | N/A | N/A | 1/1 | N/A | N/A | N/A | no Tx | N/A | N/A | N/A |
| P648 | 1/2 | N/A | 0/0* | N/A | N/A | N/A | 0/1 | N/A | N/A | N/A |
| P649 | 1/1 | N/A | 1/2 | 7/8† | N/A | N/A | no Tx | N/A | N/A | N/A |
| P650 | 0/1 | N/A | N/A | N/A | N/A | 1/1 | N/A | N/A | 1/1 | N/A |
| P656 | 2/2# | 1/2 | 1/1# | 2/2 | N/A | N/A | 2/2# | 2/2 | N/A | N/A |
| Overall | 5/8 (63%) | | 13/15 (87%) | | | | 5/6 (83%) | | | |
| Time to Cure** | 1, 2, 3, 4, 7 (med = 5.5) | | 1 × 10, 3, 9, 32 (med = 1) | | | | 1 × 3, 10, 26 (med = 6.5) | | | |
| Mean BG (mg/dL) | 261 ± 191 (n = 8) | | 145 ± 109 (n = 15) | | | | 173 ± 95 (n = 6) | | | |
| p vs PSF (2-sample t test) | 0.076 | | | | | | 0.59 | | | |

PSF = Persufflation, N/A = condition not present, no Tx = condition present but no mice transplanted.
*Diabetes reversed in both mice transplanted, but one mouse died and one did not relapse post-nephrectomy.
**Median (med) includes non-cures.
† Islets cultured for 11 days. # Islets cultured for 1 day.

*FIG. 8*

| Preservation Method | Pancreas Lobe | n | Day 0 IE Yield IE/g | Day 2 IE Recovery % | Day 2 OCR/DNA nmol/(min·mg) | Day 2 OCR Yield nmol/(min·g) |
|---|---|---|---|---|---|---|
| Immediate Isolation | Duodenal | 3 | 1384 ± 598 | 33 ± 9* | 180 ± 32 | 1.41 ± 0.27* |
| Persufflation (24 hr) | Splenic | 3 | 1455 ± 125 | 45 ± 31* | 200 ± 22 | 1.88 ± 1.35* |
| TLM (24 hr) | Connecting | 3 | 1185 ± 553 | 29 ± 32* | 174 ± 22 | 1.06 ± 0.98* |
| Immediate Isolation | Duodenal | 1 | 1313 | 27 | 159 | 1.22 |
| Persufflation (24 hr) | Splenic | 1 | 1551 | 23 | 179 | 0.93 |
| TLM (24 hr) | Connecting | 1 | 1405 | 7 | 156† | 0.36‡ |
| Immediate Isolation | Duodenal | 1 | 2016 | 39 | 164 | 1.61 |
| Persufflation (24 hr) | Splenic | 1 | 1500 | 67 | 222 | 2.83 |
| TLM (24 hr) | Connecting | 1 | 1593 | 51 | 199 | 1.76 |
| Immediate Isolation | Duodenal | 1 | 825 | analysis pending | 216 | anal. pend. |
| Persufflation (24 hr) | Splenic | 1 | 1314 | analysis pending | 199 | anal. pend. |
| TLM (24 hr) | Connecting | 1 | 556 | analysis pending | 168 | anal. pend. |

*n=2. †Day 1 value due to lack of sufficient tissue to run OCR assay on day 2.
‡Calculated using day 1 OCR/DNA value.

*FIG. 9*

PERFUSING AN ORGAN WITH AN IN SITU GENERATED GAS

CROSS-REFERENCE TO RELATED APPLICATIONS

The present application claims the benefit under 35 U.S.C. 119(e) of U.S. Provisional Patent Application No. 61/268,973, filed Jun. 18, 2009, the disclosure of which is incorporated herein by reference.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of SBIR Phase I Contract Nos. R43DK070400 and R43DK070400-02S1 awarded by NIH.

BACKGROUND OF THE INVENTION

The present invention relates generally to organ preservation for organ and tissue transplantation and relates in particular to a novel method and system for organ preservation.

Transplantation of islets of Langerhans has been investigated for its potential as a treatment for type 1 diabetes mellitus for over 30 years since the allotransplantation of islets from rats was shown to reverse chemically induced diabetes (see Ballinger et al., "Transplantation of intact pancreatic islets in rats," *Surgery*, 72(2):175-86 (1972), which is incorporated herein by reference). Several years later, it was shown that auto-transplantation of islets back to a donor was a feasible treatment to prevent the onset of diabetes in people with pancreatitis (see Najarian et al., "Total or near total pancreatectomy and islet autotransplantation for treatment of chronic pancreatitis," *Ann Surg.*, 192(4): 526-42 (1980), which is incorporated herein by reference). Successful islet allotransplantation, however, remained difficult to achieve until 2000 when the development of the Edmonton Protocol achieved success in seven consecutive patients transplanted with islets from multiple pancreata (see Shapiro et al., "Islet transplantation in seven patients with type I diabetes mellitus using a glucocorticoid-free immunosuppressive regimen," *New England Journal of Medicine*, 343(4):230-8 (2000), which is incorporated herein by reference). The aforementioned success has largely been attributed to the use of a glucocorticoid-free immunosuppression. This success was then repeated at other institutions, including the University of Minnesota, with over 500 transplants utilizing variations of the Edmonton Protocol worldwide from 2000-2006 (see Shapiro et al., "Edmonton's islet success has indeed been replicated elsewhere," *The Lancet*, 362(9391), 1242 (2003); Emamaullee et al., "Factors influencing the loss of beta-cell mass in islet transplantation," *Cell Transplantation*, 16(1):1-8 (2007), both of which are incorporated herein by reference). Islet transplantation offers several advantages over other presently utilized treatments for diabetes. Due to the innate ability of the islets to monitor and regulate glucose levels via insulin production, transplantation allows for the constant, tight control of blood glucose levels, something which cannot be achieved by patient self-monitoring. Even when tight glucose control is not fully achieved, islet transplantation is especially important in patients who exhibit hypoglycemia unawareness, the lack of physical symptoms indicative of low blood sugar. In addition, when compared to other transplant treatments, transplantation minimizes the chance of infection since the infusion of islets into the portal vein does not require open surgery.

Even though the use of islet transplantation for consistent diabetes reversal has been demonstrated, there still remain several hurdles for the widespread implementation of this therapy in a clinical setting. Although some success has been achieved with single donor transplants, most centers continue to require multiple donor organs for a single patient for various reasons including low islet yields and/or quality per donor (see Hering et al., "Single-donor, marginal-dose islet transplantation in patients with type I diabetes," *JAMA*, 293(7):830-5 (2005), which is incorporated herein by reference). There is presently a shortage of quality donor organs, which limits the number of transplants possible. With increasing interest in islet transplantation and with new centers applying to the U.S. Food and Drug Administration (FDA) for Investigational New Drug (IND) status, it is more important than ever to maximize both the number and quality of available organs. In order to do this, it is necessary to protect the islets from damage beginning at the time of organ procurement and islet processing through eventual engraftment in the transplant recipient.

One of the main challenges of pancreatic islet transplantation is acquiring viable, functional transplant tissue in sufficient quantity for successful treatment (see Iwanaga et al., "Pancreas preservation for pancreas and islet transplantation, invited review" *Current Opinion in Organ Transplantation*, 13(2):135-141 (2008), which is incorporated herein by reference). As such, it is important to: (1) maximize the donor organs that are acceptable for clinical use; (2) improve the preservation, storage, and transport of those organs to keep them acceptable; and (3) enhance the yield and quality of the islets harvested from the organ by improvements in islet isolation, culture, and storage. There appears to be a critical mass of viable islets for the success of single donor transplants, and current protocols yield transplant tissue that is generally right at the marginal edge of this critical mass.

The current protocol for pancreas procurement includes brain-dead, heart-beating donors with practically no warm ischemia (WI) time. Pancreas preservation (including transport and storage times) must be equal to or less than eight hours of cold (4-8° C.) storage. The cold storage protocols vary, with some using established cold preservation solutions (CPS), such as UW (University of Wisconsin) solution, and with others using experimental CPS or combinations of CPS. Since 2002, the two-layer method (TLM) has drawn much attention. TLM was developed as a method of pancreas preservation in the late 1980's and early 1990's (see Kuroda et al., "A new simple method for cold-storage of the pancreas using perfluorochemical," *Transplantation*, 46(3): 457-60 (1988); Fujino et al., "Preservation of canine pancreas for 96 hours by a modified two-layer (UW solution/perfluorochemical) cold storage method," *Transplantation*, 51(5):1133-5 (1991); Kuroda et al., "Oxygenation of the human pancreas during preservation by a two-layer (University of Wisconsin solution/perfluorochemical) cold-storage method," *Transplantation*, 54(3):561-2 (1992), all of which are incorporated herein by reference).

TLM involves suspending a pancreas half-way between layers of CPS and oxygenated perfluorocarbon (PFC). The basic concept is to enhance tissue oxygenation during storage by supplying greater amounts of oxygen to the organ surface due to the enhanced oxygen carrying capacity of PFC as compared to CPS. TLM gained a lot of momentum as the state of the art for pancreas preservation in the early 2000's following the development of the Edmonton Protocol, with many islet processing centers publishing on the advantages of this approach to organ preservation when compared with classical methods (see Hering et al., "Impact of two-layer pancreas preservation on islet isolation and transplantation," *Transplantation*, 74(12):1813-6 (2002); Fraker et al., "Use of oxygenated perfluorocarbon toward making every pancreas count," *Transplantation*, 74(12): 1811-2 (2002); Tsujimura et al., "Human islet transplantation from pancreases with prolonged cold ischemia using additional preservation by the two-layer (UW solution/perfluorochemical) cold-storage method," *Transplantation*, 74(12):1687-91 (2002); Lakey et al., "Preservation of the human pancreas before islet isolation using a two-layer (UW solution-perfluorochemical) cold storage method," *Transplantation*, 74(12):1809-11 (2002); Ricordi et al., "Improved human islet isolation outcome from marginal donors following addition of oxygenated perfluorocarbon to the cold-storage solution," *Transplantation*, 75(9):1524-7 (2003); Matsumoto et al., "The effect of two-layer (University of Wisconsin solution/perfluorochemical) preservation method on clinical grade pancreata prior to islet isolation and transplantation," *Transplantation Proceedings*, 36(4): 1037-9 2004; Witkowski et al., "Two-layer method in short-term pancreas preservation for successful islet isolation," *Transplantation Proceedings*, 37(8), 3398-401 (2005), all of which are incorporated herein by reference).

Much of the interest in TLM was due to the potential for use of marginal donor organs for successful transplantation. Presently, there is a shortage of suitable donor organs, and in some countries the use of heart-beating donors is prohibited due to cultural taboos. Recently, however, it has come to light that oxygenation that depends on surface diffusion, as is the case in TLM, may be insufficient to oxygenate the majority of the human pancreas. Diffusion modeling of the pancreas by a group at the University of Minnesota has demonstrated that oxygen can only penetrate the outer 1 mm of the pancreas (see Papas et al., "Pancreas oxygenation is limited during preservation with the two-layer method," *Transplantation Proceedings*, 37(8), 3501-4 (2005), which is incorporated herein by reference). Additionally, several islet transplantation centers have very recently released retrospective data demonstrating that there is no significant improvement in islet isolation or transplantation outcome when the pancreas is preserved by TLM vs. classical storage in CPS (UW) alone (see Kin et al., "Islet isolation and transplantation outcomes of pancreas preserved with University of Wisconsin solution versus two-layer method using preoxygenated perfluorocarbon," *Transplantation*, 82(10): 1286-90 (2006); Caballero-Corbalan et al., "No beneficial effect of two-layer storage compared with UW-storage on human islet isolation and transplantation," *Transplantation*, 84(7):864-9 (2007), both of which are incorporated herein by reference).

In view of the above, there clearly remains a compelling need for improved methods of pancreas preservation.

For other human organs, passive cold storage in CPS is common and reported in the peer-reviewed literature. There are also some published protocols and commercial equipment for liquid perfusion preservation of organs. In both of these methods, provision of oxygen is minimal and can be inadequate for optimal organ preservation.

SUMMARY OF THE INVENTION

It is an object of the present invention to provide a novel method of pancreas preservation.

Therefore, according to one aspect of the invention, there is provided a method of pancreas preservation, said method of pancreas preservation comprising perfusing the pancreas with a preserving gas. The pancreas may be, for example, human or porcine. The perfusion of the pancreas may be anterograde, retrograde, ductal, anterograde/ductal, or retrograde/ductal. The preserving gas used to perfuse the pancreas may be dissolved in a liquid solvent and then administered as such to the pancreas or may be mixed with one or more other gases and then administered as such to the pancreas. Examples of the preserving gas may include, but are not limited to, oxygen gas, hydrogen gas, carbon dioxide gas, carbon monoxide gas, and water vapor. The preserving gas may be generated in situ by electrochemical or other means. For example, where the preserving gas is oxygen, the preserving gas may be generated in situ using an electrochemical oxygen concentrator. Alternatively, where the preserving gas is oxygen and/or hydrogen, the preserving gas may be generated in situ using an electrolyzer. Alternatively, where the preserving gas is oxygen, the preserving gas may be generated in situ by pressure swing adsorption or by chemical oxygen release (e.g., by burning a perchlorate or oxygen candle).

It is another object of the present invention to provide a novel method of organ preservation.

Therefore, according to another aspect of the invention, there is provided a method of organ preservation, said method of organ preservation comprising (a) generating in situ a preserving gas; and (b) perfusing one or more organs with the in situ generated preserving gas. The one or more organs may be, for example, the pancreas, the liver, the kidney, the heart, the lung, or the small intestine. Where the organ is a pancreas, the pancreas may be, for example, human or porcine. The at least one preserving gas used to perfuse the one or more organs may be dissolved in a liquid solvent and then administered as such to the one or more organs or may be mixed with one or more other gases and then administered as such to the one or more organs. Examples of the preserving gas may include, but are not limited to, oxygen gas, hydrogen gas, carbon dioxide gas, carbon monoxide gas, and water vapor. The preserving gas may be generated in situ by electrochemical or other means. For example, where the preserving gas is oxygen, the preserving gas may be generated in situ using an electrochemical oxygen concentrator. Alternatively, where the preserving gas is oxygen and/or hydrogen, the preserving gas may be generated in situ using an electrolyzer. Alternatively, where the preserving gas is oxygen, the preserving gas may be generated in situ by pressure swing adsorption or by chemical oxygen release (e.g., by burning a perchlorate or oxygen candle). Where an electrochemical oxygen concentrator is used to generate oxygen gas, a vapor feed may be used to supply water to the electrochemical oxygen concentrator.

It is still another object of the present invention to provide a novel system for organ preservation, said system comprising (a) an organ storage container for storing an organ; (b) a thermal control device for maintaining the contents of the organ storage container at a desired temperature; (c) means for in situ generating a preserving gas; and (d) means for delivering the preserving gas to the contents of said organ storage container in a plurality of gas streams, said plurality of gas streams having independently adjustable flow rates.

Additional objects, as well as aspects, features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts:

FIGS. 5(a) through 5(c) are images of dithizone-stained islets isolated from pancreata, as discussed in Example 1, which were exposed to (a) no preservation, (b) 6 hours of persufflation preservation, and (c) 6 hours of the TLM preservation;

FIG. 6 is a table, comparing preservation methods based on islet yield and quality;

FIG. 8 is a table, comparing preservation methods based on the nude mouse bioassay;

FIG. 9 is a table, comparing islet isolation outcomes between 24-hour preservation by persufflation, 24-hour preservation by TLM, and no preservation (Day 2 is defined as 48-72 hours post-isolation. The first three lines are averages of the following three sets of data.)

DETAILED DESCRIPTION OF THE INVENTION

Figure 1:
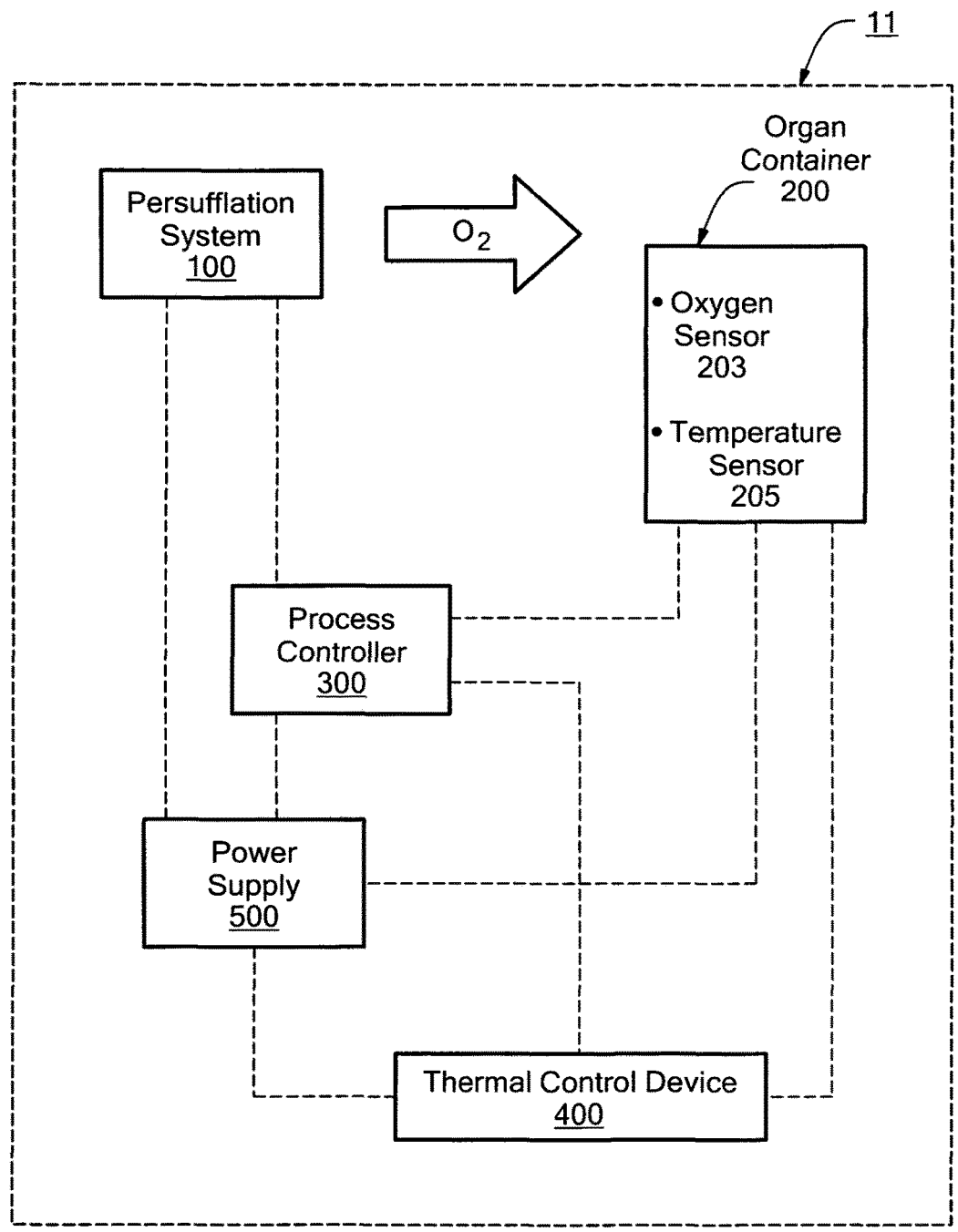
FIG. 1 is a block diagram of a first embodiment of an organ preservation system constructed according to the teachings of the present invention.

The present invention is directed at a novel method and system for organ preservation. According to one aspect of the invention, a method for organ preservation is provided, said method comprising the steps of (a) generating in situ a preserving gas; and (b) perfusing the organ with the in situ generated preserving gas. The organ may be, for example, the pancreas, the liver, the kidney, the heart, the lung, or the small intestine, and, if desired, a plurality of these organs may be perfused simultaneously. Where the organ is a pancreas, the pancreas may be, for example, human or porcine, and perfusion of the pancreas may be anterograde (i.e., orthograde), retrograde, ductal, anterograde/ductal, or retrograde/ductal. The preserving gas used to perfuse the organ may be dissolved in a liquid and then administered to the organ as a gas/liquid solution or may be dissolved in ambient air or one or more other gases and then administered to the organ as a gas/gas mixture (perfusion with a gas or with a gas/gas mixture alternatively being referred to herein as "persufflation").

Examples of the preserving gas may include, but are not limited to, gaseous oxygen (which is a nutrient needed by cells), gaseous hydrogen (which may act to protect cells by its antioxidant and antiapoptotic properties (see Wood et al., "The hydrogen highway to reperfusion therapy," *Nature Medicine,* 13(6):673-4 (2007); Ohsawa et al., "Hydrogen acts as a therapeutic antioxidant by selectively reducing cytotoxic oxygen radicals," *Nature Medicine,* 13(6):688-94 (2007)), gaseous carbon dioxide (which may regulate metabolism), gaseous carbon monoxide (which may have anti-inflammatory and antiapoptotic effects (see Wang et al., "Donor Treatment with carbon monoxide can yield islet allograft survival and tolerance," *Diabetes,* 54(5):1400-6 (2005)), and water vapor. The preserving gas may be generated in situ by electrochemical or other means. For example, where the preserving gas is oxygen, the preserving gas may be generated in situ using an electrochemical oxygen concentrator. Alternatively, where the preserving gas is oxygen and/or hydrogen, the preserving gas may be generated in situ using an electrolyzer. Alternatively, where the preserving gas is oxygen, the preserving gas may be generated in situ by pressure swing adsorption or by chemical oxygen release (e.g., by burning a perchlorate or oxygen candle).

The additional use of cell culture media or organ preservation solution rinses or baths to the organ surface or to ductal or vasculature systems may also be incorporated to enhance the quality of the organ during organ preservations by persufflation (see Saad et al., "Extension of ischemic tolerance of porcine livers by cold preservation including postconditioning with gaseous oxygen," *Transplantation,* 71(4):498-502 (2001), which is incorporated herein by reference). The addition of antioxidant rinses to the persufflation protocol can also be used to improve the quality of the organ during organ preservation. In addition, nutrients, antioxidants or other preserving agents can be added in aerosol form during persufflation.

As noted above, where, for example, the organ being preserved is a human or porcine pancreas, one may persufflate the pancreas through one or more arteries, through one or more veins, through one or more ducts, through a combination of arteries and ducts, or through a combination of veins and ducts. For example, in the case of a human pancreas, persufflation may be anterograde via cannulation of one or more of the following vessels: (i) en bloc pancreaticoduodenectomy and/or splenectomy with division of aorta to include celiac trunk and superior mesenteric artery; (ii) en bloc pancreaticoduodenectomy and/or splenectomy with direct cannulation of celiac trunk and superior mesenteric artery; and (iii) en bloc pancreaticoduodenectomy and/or splenectomy with direct cannulation of proximal splenic artery and superior mesenteric artery. Alternatively, persufflation may be retrograde via cannulation of the following vessels: (i) en bloc pancreaticoduodenectomy and/or splenectomy with cannulation of inferior mesenteric vein or splenic vein; (ii) en bloc pancreaticoduodenectomy and/or splenectomy with cannulation of superior mesenteric vein;

and (iii) en bloc pancreaticoduodenectomy and/or splenectomy with cannulation of portal vein.

Alternatively, in the case of a porcine pancreas, persufflation may be anterograde via cannulation of one or more of the following vessels: (i) en bloc pancreaticoduodenectomy and/or splenectomy with division of aorta to include celiac trunk and superior mesenteric artery; (ii) en bloc pancreaticoduodenectomy and/or splenectomy with direct cannulation of celiac trunk and superior mesenteric artery; and (iii) en bloc pancreaticoduodenectomy and/or splenectomy with direct cannulation of proximal splenic artery and superior mesenteric artery. Alternatively, persufflation may be retrograde via cannulation of the following vessels: (i) en bloc pancreaticoduodenectomy and/or splenectomy with cannulation of splenic vein; (ii) en bloc pancreaticoduodenectomy and/or splenectomy with cannulation of superior mesenteric vein; and (iii) en bloc pancreaticoduodenectomy and/or splenectomy with cannulation of inferior mesenteric vein; and (iv) en bloc pancreaticoduodenectomy and/or splenectomy with cannulation of portal vein.

In the case of a liver, persufflation may be anterograde via cannulation of one or more of the following vessels: (i) common hepatic artery; (ii) proper hepatic artery; and (iii) portal vein. Alternatively, persufflation may be retrograde via cannulation of one or more of the following vessels: (i) hepatic vein(s); and (ii) infra- or suprahepatic inferior vena cava.

Where, for example, the in situ generated preserving gas consists of pure gaseous oxygen, it may be desirable to dilute the gaseous oxygen in a liquid solvent, such as water or a water-based solvent, and to perfuse the organ with the gas/liquid solution, or it may be desirable to dilute the gaseous oxygen with another gas or with other gases, such as ambient air, and to persufflate the organ with the gas/gas mixture. In the case of perfusion with a gas/liquid solution, the concentration of gaseous oxygen in the solution may be at about the point of liquid saturation, which may be around 0.3-1 atm of partial pressure. In addition, the flow rate of the solution to the organ may be, for example, about 200 cc/min or greater. In the case of persufflation, the concentration of gaseous oxygen in the mixture may be about 20-100%, more preferably about 30-80%, even more preferably about 40%. In addition, the flow rate of the mixture to the organ may be, for example, approximately 10-60 cc/min, preferably 15-22 cc/min, and the gas pressure of the administered solution may be, for example, no more than about 22 mm Hg. In certain cases, preservation of an organ may be enhanced if persufflation is performed at reduced temperatures, such as approximately 4-8° C.

Where the organ being preserved is a pancreas, systemic heparinization of the pancreas with 100,000 units at least 5 minutes prior to death is preferably performed to prevent small clots from forming throughout the pancreas. In addition, the organ should be flushed with 5 liters of a heparinized cold preservation solution during procurement to prime it for preservation, to purge any remaining blood from the vasculature, and to accelerate bulk organ cooling, which reduces the exposure of core regions of the pancreas to ischemia at elevated temperatures (>8° C.). Following procurement, the organ should be extensively tested for leaks by flushing cold preservation solution through the vasculature, and any leaks found should be tied. The pancreas and attached vasculature should then be allowed to float freely in the cold preservation solution to prevent any kinking of the vasculature, especially at the sites of cannulation. Any remaining minor leaks should be identified by the presence of bubbles emerging from the vasculature to ensure that all the gas is flowing through the pancreas, and these leaks should be tied. The access points for cannulation are discussed above. Other organs may also benefit from heparinization.

With the present method of procurement, the vast majority of the pancreas is flushed with cold preservation solution, thereby clearing a path for whole organ persufflation. Histological sectioning of organs procured with this technique showed no red blood cells present in tissue preserved by either persufflation or TLM due to more thorough flushing. No noticeable differences were observed by histology between organ samples collected immediately following procurement (t=0) and those collected following 6 or 24 hours of persufflation. However, tissue preserved with TLM exhibited increased necrosis/autolysis and a high incidence of pyknotic nuclei when compared with persufflated samples, especially after 24-hour preservation.

The method of the present invention may enable implementation with human pancreata and with porcine pancreata for xenotransplantation. Methods to enhance preservation of pancreata with resulting improvements in islet yield and quality and ultimately in clinical outcome are urgently needed to move the field of islet transplantation forward into established medical practice. Arterial persufflation of the pancreas during storage to provide oxygen throughout the organ at the capillary level is shown herein to be a feasible technique. In particular, the feasibility of supplying electrochemically generated oxygen at the proper flow rates and pressures for persufflation of the porcine and human pancreas has been demonstrated. The results show the promise of this technique, as compared to no preservation and as an improvement over TLM storage.

Two applications of the present method in pancreas preservation are as follows: (1) oxygen persufflation throughout cold preservation (from donor organ harvest until islet isolation) with the goal of extending the cold preservation time beyond the current standard of 8 hours to increase the donor pool and ease the logistics of organ and islet procurement; and (2) oxygen persufflation (~3 hours) after organ transport with standard cold storage (~12 hours of TLM) as a recovery method to enhance islet yield and quality at the islet processing center. These two applications involve improving the islet yield and quality and/or storage time for pancreata from standard donors. In one application, the pancreas is persufflated for the whole storage time; in the second application, persufflation is used as a recovery treatment after standard cold storage. (Note that in pancreas preservation, there is almost always a trade-off between preservation time and islet yield and quality.) Increased storage time (at similar islet yield and quality) can lead to procedural flexibility and use of more organs. Increased islet yield and quality (at current storage times) may have a greater impact on individual transplant outcomes. An entirely separate branch of application, that would also be extremely valuable if successful, would be to use persufflation to enhance organ quality and, thus, to improve organ supply for the donor after cardiac death category.

Referring now to FIG. 1, there is shown a block diagram of one embodiment of an organ preservation system constructed according to the teachings of the present invention, said organ preservation system being represented generally by reference numeral 11.

Organ preservation system 11 may comprise a persufflation system 100, an organ container 200, a process controller 300, a temperature control device 400, and a power supply 500.

Figure 2:
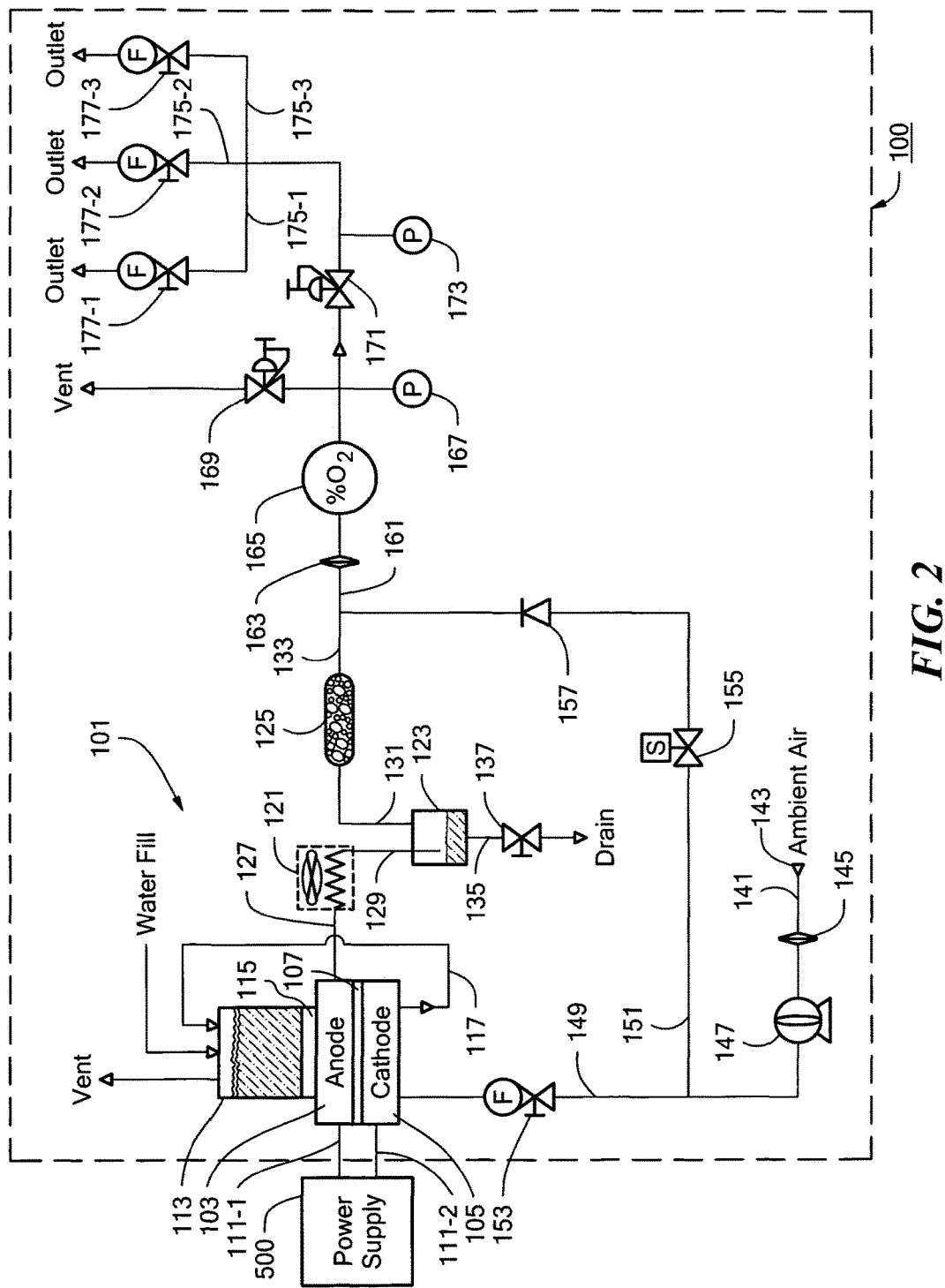
FIG. 2 is a schematic diagram of one embodiment of the persufflation system shown in FIG. 1, the persufflation system being shown together with the power supply.

Referring now to FIG. 2, persufflation system 100 is shown in greater detail, persufflation system 100 being shown together with power supply 500. Persufflation system 100 may comprise an electrochemical oxygen concentrator (EOC) 101. EOC 101, the details of which are discussed in greater detail below, may comprise a single oxygen-concentrator cell or a plurality of series- or parallel-connected oxygen-concentrator cells. Each of said one or more oxygen-concentrator cells may comprise an anode 103 and a cathode 105, anode 103 and cathode 105 being in intimate contact with and separated by an ionically-conductive separator 107. Separator 107 may be, for example, a solid proton-exchange membrane (PEM), such as a NAFION® NRE-1135 membrane (E.I. du Pont de Nemours & Company, Wilmington, Del.). Anode 103 and cathode 105 may be electrically coupled to power supply 500 using electrical leads 111-1 and 111-2, respectively, and may also be coupled by means not shown to process controller 300 (not shown in FIG. 2). (Additional components of persufflation system 100 may be coupled to power supply 500 and/or process controller 300, but these connections are not shown herein for clarity.)

As shown below, EOC 101 may be used to concentrate oxygen from ambient air.

Anode: $2H_2O \leftrightarrow 4H^+ + 4e^- + O_2(pure)$     [1]

Cathode: $O_2(air) + 4H^+ + 4e^- \leftrightarrow 2H_2O$     [2]

Net: $O_2(air)@cathode \leftrightarrow O_2(pure)@anode$     [3]

EOC 101 may additionally comprise a water reservoir 113 for holding a quantity of water to be supplied to anode 103. As will be described further below, a pervaporation membrane 115, which may be, for example, a NAFION® NRE-1135 membrane, may be positioned between a bottom outlet of water reservoir 113 and anode 103, pervaporation membrane 115 serving to steadily feed vapor phase water to anode 103 while preventing oxygen produced at anode 105 from mixing with the water. In other words, this arrangement allows water to be fed passively to anode 103 while the product oxygen is allowed to flow out of the anode edgewise through a flowfield gap. It is believed that the above-described vapor feed system is advantageous, as compared to a corresponding liquid feed system, in that the present vapor feed system keeps many impurities that may be present in the water supply from being fed to anode 103. For example, where tap water is used as the water supply, there may be halogen, alkali metals, alkaline earth metals, transition metal elements, organic compounds and/or microorganisms present in the water. These elements, compounds and/or microorganisms, if carried to the active elements of EOC 101, can lead to performance and efficiency degradation of the EOC due to, for example, membrane contamination or catalyst poisoning. These materials could also be detrimental to the organ being preserved. Pervaporation membrane 115 effectively limits access of these species to the active elements of EOC 101 and the downstream preserved organ, and effectively allows an in situ distillation of the reservoir water.

EOC 101 may additionally comprise a recuperation tube 117 coupled at one end to cathode 105 and at the opposite end to reservoir 113, recuperation tube 117 being used to conduct water produced at cathode 105 to reservoir 113. In this way, the frequency with which water needs to be added to the system is reduced.

Persufflation system 100 may further comprise means for cooling and drying the gaseous oxygen produced at anode 103. In the present embodiment, said cooling and drying means may comprise an oxygen cooler 121, an oxygen/water separator 123, and an oxygen drier or desiccant 125. A fluid line 127 may be connected at one end to an outlet of anode 103 and at the other end to an inlet of oxygen cooler 121. In addition, a fluid line 129 may be connected at one end to an outlet of oxygen cooler 121 and at the other end to an inlet of oxygen/water separator 123. Additionally, a fluid line 131 may be connected at one end to an outlet of oxygen/water separator 123 and at the opposite end to an inlet of oxygen drier 125. Moreover, a fluid line 133 may be connected at one end to the outlet of oxygen drier 125. A fluid line 135 for draining oxygen/water separator 123 may be connected to the bottom of oxygen/water separator 123, and a drain valve 137 may be connected to the outlet end of fluid line 135.

Persufflation system 100 may further comprise ambient air supply means. In the present embodiment, said ambient air supply means may comprise a fluid line 141, fluid line 141 having an inlet 143 for the entry thereinto of ambient air. An air filter 145 may be positioned along line 141 to remove certain impurities from the ambient air. Air filter 145 may be of the type that physically captures particles (for example, a 10 micron pore size filter) or may be of the type that chemically captures or modifies particles (for example, a carbon or permanganate filter.) An air pump 147 for pumping air through line 141 (both to supply air to cathode 105 and to dilute oxygen produced by EOC 101) may be positioned along line 141 downstream of air filter 145. Downstream of air pump 147, line 141 may branch into a fluid line 149 and a fluid line 151. A valve 153, which may also include a flow-rate indicator, may be positioned along line 149, with the outlet of line 149 being appropriately positioned to supply cathode 105 with air. An adjustable flow valve 155 may be positioned along line 151 to regulate the flow of air through line 151 and, in so doing, to adjust the rate at which ambient air is to be mixed with pure oxygen so that a desired oxygen concentration may be obtained. A check valve 157 may be positioned along line 151 downstream of valve 155.

Persufflation system 100 may further comprise a fluid line 161 coupled to the outlets of lines 133 and 151 for combining the pure oxygen from line 133 with the ambient air of line 151. A medical grade filter 163, which may have, for example, a pore size of 0.2 micron, may be positioned along line 161. An oxygen concentration sensor 165 may be positioned along line 161 downstream of filter 163. A pressure transducer/gauge 167 and a pressure relief valve 169 may be positioned along line 161 downstream of sensor 165. A pressure regulator 171 may be positioned along line 161 downstream of transducer/gauge 167 and valve 169. A pressure transducer gauge 173 may be positioned along line 161 downstream of gauge 173. Downstream of gauge 173, line 161 may branch into lines 175-1, 175-2 and 175-3. A valve with flow rate indicator 177-1 may be positioned at the outlet end of line 175-1, a valve with flow rate indicator 177-2 may be positioned at the outlet end of line 175-2, and a valve with flow rate indicator 177-3 may be positioned at the outlet end of line 175-3.

Therefore, as can be seen, persufflation system 100 enables up to three different substreams of preserving gas to be administered to the organ, with each of the three different substreams having independently adjustable flow rates. In addition, it should also be noted that the oxygen concentration and maximum delivery pressure of the three substreams may be adjusted, albeit not independently relative to one another. Additional pressure regulators or mass flow controllers may be employed in these substreams to provide further independent pressure and flow regulation for each substream. Moreover, if desired, persufflation system 100 has the capability of producing gas that is humidified, for example, by the omission of oxygen drier 125.

Figure 3:
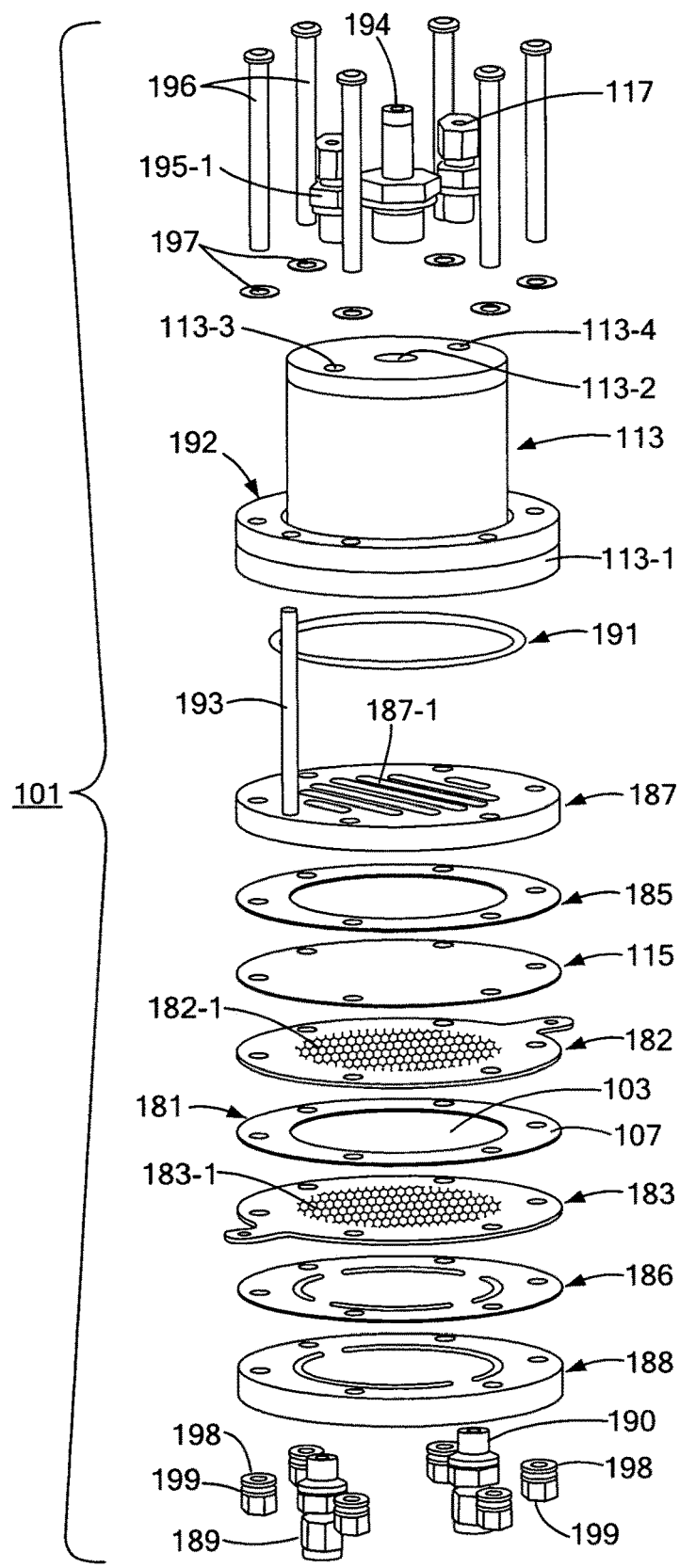
FIG. 3 is partially exploded perspective view of one embodiment of the electrochemical oxygen concentrator shown in FIG. 2.

Referring now to FIG. 3, EOC 101 is shown in greater detail. As can be seen, EOC 101 may comprise a membrane electrode assembly 181. Assembly 181, in turn, may comprise anode 103, separator 107, and cathode 105 (which is not shown in FIG. 3 but is positioned opposite anode 103 on the underside of separator 107). EOC 101 may further comprise an anode collector 182 and a cathode collector 183. Anode collector 182, which may have a porous central region 182-1 defining a fluid diffusion chamber, may be positioned against the top surface of anode 103, and cathode collector 183, which may have a porous central region 183-1 defining a fluid diffusion chamber, may be positioned against the bottom surface of the cathode. EOC 101 may further comprise pervaporation membrane 115, which may be positioned against the top surface of anode collector 182. As explained above, pervaporation member 115 may be used to feed water in a vapor phase to anode 103.

EOC 101 may further comprise an annular anode gasket 185 and a cathode insulator 186. Gasket 185 may be positioned against the top surface of pervaporation membrane 115, and cathode insulator 186 may be positioned against the bottom surface of cathode collector 183. EOC 101 may further comprise an anode endplate 187 and a cathode endplate 188. Anode endplate 187, which may comprise a porous central region 187-1, may be positioned against anode gasket 185, and cathode endplate 188 may be positioned against cathode insulator 186.

EOC 101 may further comprise a cathode inlet port 189 and a cathode outlet port 190, inlet port 189 and outlet port 190 being mechanically coupled to cathode endplate 188 and being fluidly coupled to the cathode.

EOC 101 may further comprise water reservoir 113, which may be positioned over anode endplate 187. A water reservoir O-ring 191 may be seated on anode endplate 187 and may be used to form a fluid seal for the water passing from reservoir 113 to porous central region 187-1 of anode endplate. An anode clamp ring 192 may be mounted on a peripheral flange 113-1 of reservoir 113.

EOC 101 may further comprise an oxygen outlet tube 193 for conducting gaseous oxygen away from anode 103, tube 193 being mounted at one end on anode endplate 187 and extending through flange 113-1 of reservoir 113 and anode clamp ring 192.

EOC 101 may further comprise a water fill port 194, which may be coupled to reservoir 113 through an opening 113-2, a reservoir vent port 195-1, which may be coupled to reservoir 113 through an opening 113-3, and recuperation tube 117, which may be coupled to reservoir 113 through an opening 113-4.

EOC 101 may further comprise hardware for mechanically coupling together many of the above-described components. Such hardware may comprise a plurality of cell assembly bolts 196, as well as corresponding pluralities of washers 197, Belleville washers 198 and nuts 199.

Referring back now to FIG. 1, organ container 200 may be suitably dimensioned to store a desired organ and may comprise an opening (not shown) through which tubes coupled to the outlets of valves 177-1, 177-2 and 177-3 may be passed to deliver the gaseous oxygen solution produced by persufflator system 100 to the organ stored in container 200. In addition, the interior of organ container 200 may be provided with an oxygen sensor 203 or other gas sensors and a temperature sensor 205, sensors 203 and 205 being used to provide oxygen, gas and/or temperature readings, respectively, to process controller 300 for feedback control.

Controller 300 may comprise an embedded controller with a keypad/LCD user interface to manage the various system components and to facilitate user control. Two closed-loop controls may be incorporated to allow self-regulation of process conditions, one for EOC cell current and the other for post-dilution oxygen concentration. A current sensor and a variable voltage DC-DC converter may be used in conjunction with a software-based proportional-integral control algorithm to control the EOC cell current (and, therefore, the pure oxygen production rate) to the amount required by the user's total flow and oxygen concentration requirements. Similarly, controller 300 may also be used, in conjunction with oxygen sensor 203 and valve 155 to control the extent of air/oxygen mixing to achieve the desired oxygen concentration setpoint. The embedded controller also may be used to provide real-time readings to the user of system relief and manifold delivery pressures.

Thermal control device 400 may comprise, for example, a commercially-available thermoelectric based (or Peltier) chest, such as the VECTOR® thermoelectric cooler. Vapor-compression refrigeration or physical chilling from ice or other coolants may be used instead of thermoelectrics; however, in the event that one wishes to supply heat to organ container 200, as opposed to lowering the temperature of organ container 200, the bidirectional heat pumping capability of thermoelectrics makes this possible in a way that vapor-compression refrigeration or physical chilling does not.

Power supply 500 may comprise, for example, a battery pack module housing two 24V nickel-metal hydride (NiMH) batteries, a charger for these batteries, a 24V DC-DC converter (for regulation) and a battery shut-off circuit to prevent deep battery discharge.

Figure 4:
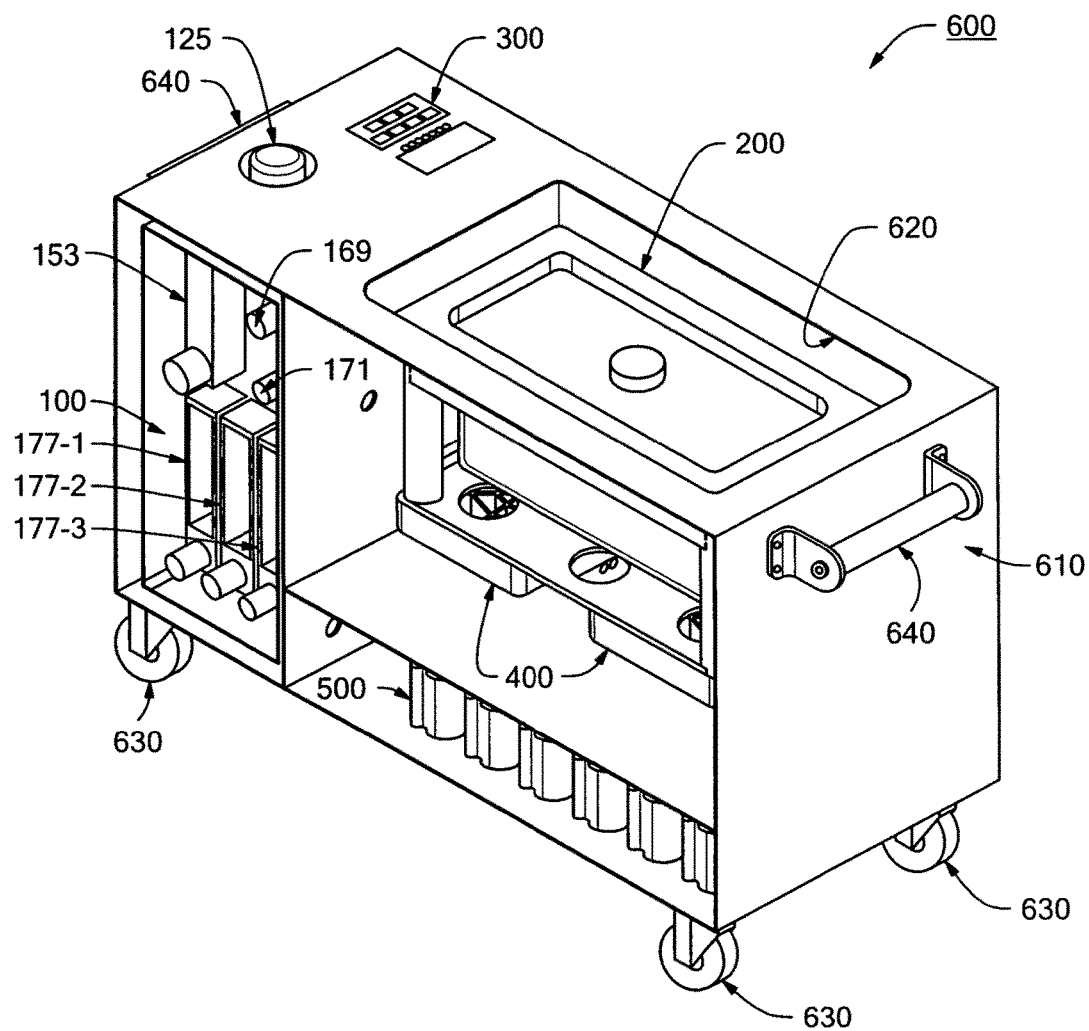
FIG. 4 is a perspective view of a second embodiment of an organ preservation system constructed according to the teachings of the present invention.

Referring now to FIG. 4, there is shown a perspective view of a second embodiment of an organ preservation system constructed according to the teachings of the present invention, said organ preservation system being represented generally by reference numeral 600. (Certain components of system 600 are not shown for clarity or simplicity.) This embodiment is shown as a portable system.

System 600 is similar in many respects to system 11, system 600 comprising persufflation system 100, organ container 200, process controller 300, thermal control device 400, and power supply 500. System 600 may further comprise a thermally-insulated housing 610, in which persufflation system 100, organ container 200, process controller 300, thermal control device 400, and power supply 500 may be disposed. (A side wall of housing 610 is not shown to reveal some of the components disposed in the interior of housing 610, and a removably mounted insulated lid to housing 610 is not shown to reveal the top of organ container 200 and an opening 620 through which organ container 200 may be removably inserted.) Without wishing to be limited to any particular dimensions, housing 610 may have a footprint similar to that of a picnic cooler (e.g., 12" H×10" D×22" W). Casters 630 and handles 640 may be mounted on housing 610 to facilitate the transportation of system 600.

System 600 may further comprise a logging/diagnostic functionality. This feature would allow a system user to view and record the system process readings (pressure, concentration, temperature, etc., which may not be available at the on-board controller interface) via download to an external computer at the completion of the storage time. All of the power conditioning circuitry, relays, and certain sensor transducers may be integrated into a unitized circuit board.

A heat pump may require non-standard or variable DC electrical power to operate the Peltier devices, which would require the identification of an appropriate power supply. This design may include battery design for 24 hours of operation, with optional AC converter and onboard battery charger. The batteries may be NiMH rechargeable batteries as they are lower cost, safer and more convenient than lithium ion batteries and have a reasonable energy storage density.

The examples below are illustrative only and do not limit the present invention.

EXAMPLE 1

Demonstration of Improved Islet Persufflation Oxygenation Method with Electrochemical Oxygen Generation The impact of persufflation on islet isolation was tested in five (5) organs by dividing each organ into its 3 lobes, taking the duodenal lobe for immediate isolation, preserving the splenic lobe for 6 hours with persufflation, and preserving the connecting lobe for 6 hours with TLM. In one experiment, preservation was extended to 24 hours. The persufflation system utilized an EOC having an active catalyzed area of 40-cm$^2$ and employing NAFION® NRE-112 membrane as separator 107 and water pervaporation membrane 115. Anode 103 and cathode 105 comprised sprayed ink decals applied to separator 107 having 4 mg/cm$^2$ loading of platinum-iridium black catalyst and platinum black catalyst, respectively. With deionized water provided to the EOC reservoir and air provided to cathode at 300 ccm, both at 21° C., the performance of this EOC was 0.84 volts at 8 amperes (200 mA/cm$^2$) and 0.93 volts at 12 amperes (300 mA/cm$^2$). The persufflation system was further configured as shown in FIG. 2. Persufflation of single pancreas lobes was with 40% oxygen at 15-22 ccm and a pressure of ~20 mm Hg, which required an EOC current of 0.94-1.4 amperes. The method of separating each organ into its lobes was chosen to allow paired comparison of the preservation methods by eliminating the donor variability. With the small sample size of five organs, it was decided to standardize (rather than randomize) the lobe used for each condition.

Organs were macroscopically assessed following procurement and immediately prior to islet isolation. All lobes exhibited thorough flushing and good texture following procurement. It was observed, however, that persufflated organs subjectively 'looked' and 'felt' better (firmer, fresher) to the surgeons performing enzymatic distension during isolation when compared with lobes preserved by TLM. This was especially evident for the organ which was preserved for 24 hours prior to isolation.

The first important observation and data showing improvement with persufflation storage related to islet morphology. As seen in FIG. 5, the persufflation-preserved porcine pancreata yielded the most morphologically well-preserved islets; fragmentation was extensive in the islets isolated from the TLM stored fragmentation was extensive in the islets. (Dithizone is an insulin stain, staining for β cells within islets.)

Table 1 below shows that islets from persufflated organs had a better average morphology score than those from TLM-stored and even fresh (t=0) organs; in paired t-test comparisons, the improvement of persufflation-preserved (PSF) over TLM was statistically significant (p=0.008).

TABLE 1

Morphology score for islets on Day 0 after isolation.

| Porcine Pancreas ID | Preservation Time | Day 0 Morphology Score | | |
|---|---|---|---|---|
| | | t = 0 | PSF | TLM |
| P647 | 6 Hrs. | | 3.0 | 2.0 |
| P648 | 6 Hrs. | 7.0 | 7.5 | 7.0 |
| P649 | 6 Hrs. | 5.0 | 7.5 | 6.0 |
| P650 | 24 Hrs. | 6.0 | 6.0 | 4.0 |
| P656 | 6 Hrs. | 6.0 | 9.0 | 7.0 |
| Average | | 6.0 | 6.6 | 5.2 |
| Std Dev | | 0.82 | 2.3 | 2.2 |
| Paired t-Test Comparison | | | 0.134 | 0.0086 |

Overall, islets from porcine lobes stored with persufflation-preservation showed superior morphology to those isolated shortly after procurement or to those from lobes stored with the TLM. FIG. 6 summarizes various measures of islet quantity and quality from the porcine pancreata preserved by various methods. Oxygen consumption rate (OCR) measurement has been shown to be a rapid, simple, quantitative, prospective assay for islet quality assessment (see Papas et al., "Human islet oxygen consumption rate and DNA measurements predict diabetes reversal in nude mice," *American Journal of Transplantation*, 7(3):707-13 (2007); Papas et al., "A stirred microchamber for oxygen consumption rate measurements with pancreatic islets," *Biotechnology and Bioengineering*, 98:1071-82 (2007); Koulmanda et al., "Islet oxygen consumption rate as a predictor of in vivo efficacy post-transplantation," *Xenotransplantation*, 10(5):484 (2003), Papas et al., "Islet quality assay based on oxygen consumption rate and DNA measurements predicts graft function in mice," *Cell Transplantation*, 12:176-176 (2003); Papas et al., "Rapid Islet Quality Assessment Prior to Transplantation," *Cell Transplantation*, 10(6): 519 (2001) and was performed as one of the measures in this work, along with standard islet equivalent count, DNA measurement, and fragmentation assessment. The measures presented in FIG. 6 are briefly defined below:

Day 0 IE yield: Islet equivalent by count per gram of digested tissue. An islet equivalent (IE) is a unit of volume, equal to that of a 150 μm diameter sphere.

Day 2 IE Recovery %: % IE by count on day 2 compared to day 0 (Day 2 count would be Day 0 IE Yield multiplied by the IE Recovery %).

Day 2 OCR/DNA: Islet Oxygen Consumption Rate (OCR) in (nmol/min) is a measure of the amount of viable islet quantity; DNA (mg) is a measure of total islet quantity; OCR/DNA is thus the ratio of viable islet quantity to total islet quantity and is a measure of islet viability.

Day 2 OCR Yield: Amount of viable islet tissue [Islet OCR (nmol/min)] per weight of digested tissue (g).

Day 2 Fragmentation Ratio: The fraction of islet equivalents calculated from the DNA measurement (1 DNA IE=10.4 ng DNA) and the IE by count. A measurement of preparation quality; there are indications that fragmented islets are less likely to survive transplant and provide insulin.

Day 2 IE Based OCR Yield: An OCR Yield (OCR/g of digested tissue) for unfragmented islets.

Figures 7A, 7B, 7C:
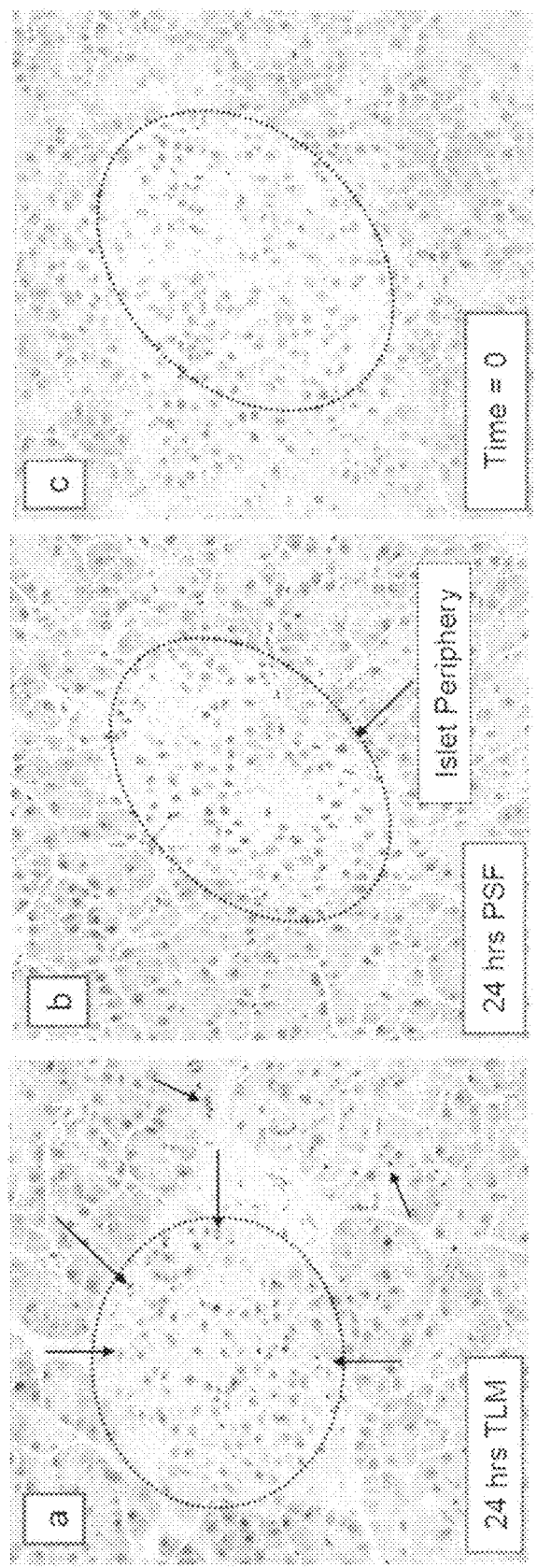
FIGS. 7(a) through 7(c) are photomicrographs of sections of porcine pancreata (a) following 24 hours of preservation with the TLM, (b) following 24 hours with persufflation; and (c) at time=0 (immediately after procurement), respectively.

As can be seen, key persufflation storage outcomes were superior to those obtained with immediate isolation and TLM storage. However, due to the small number of pancreata and the intrinsic, large donor-to-donor (and/or isolation-to-isolation) variability, most differences were not statistically significant. OCR/DNA, a measure of viability, was consistently higher with persufflation after 2 days of culture, resulting in a trend towards statistical significance versus TLM for 6-hour preservation (p=0.090, n=4) and in statistical significance for 6- and 24-hour preservation lumped together (p=0.036, n=5). The last column in FIG. 6 shows the superiority of persufflation in OCR yield associated with counted islets (calculated using the IE counts), which is a measure of the total viable intact islet tissue after culture. This superiority is partly due to the lower islet fragmentation observed with persufflation, expressed by the ratio of DNA IE (1 DNA IE=10.4 ng DNA) to IE counts. This fragmentation is reflected in photomicrographs taken from islet count samples, as seen in FIGS. 7(a) through 7(c). (Note the numerous pyknotic nuclei (arrows) in the TLM stored pancreas (FIG. 7(a)) indicating apoptotic or necrotic cell death. Pyknotic nuclei were present in pancreatic islets as well as exocrine tissue. This feature is much less apparent in the persufflated (FIG. 7(b)) and control (t=0) pancreas (FIG. 7(c)).) Importantly, the advantages of persufflation over TLM were consistent and appeared to be even more pronounced after 24-hours of preservation (single experiment).

The transplantation of islets into nude mice in the nude mouse bioassay (NMB) is a "gold standard" test for pancreatic islet function (see Ricordi et al., "Challenges toward standardization of islet isolation technology," *Transplant Proc.*, 33:1709 (2001); Ichii, et al., "A novel method for the assessment of cellular composition and beta-cell viability in human islet preparations," *Am. J. Transplant*, 5(7):1635-45 (2005); Wonnacott, "Update on regulatory issues in pancreatic islet transplantation," *Am. J. Ther.*, 12:600-4 (2005); Papas et al., "Human islet oxygen consumption rate and DNA measurements predict diabetes reversal in nude mice," *American Journal of Transplantation*, 7(3):707-13 (2007)). The five (5) porcine islet isolations after persufflation used the NMB for experimental and control conditions as budget and islet availability permitted. All data are summarized in FIG. 8. The main data set is the diabetes reversal rate: number of mice with sustained normglycemia (blood glucose <200 mg/dl) compared to the number of mice treated. It is important to note that for transplantation purposes only intact islets are selected (per assay protocol); therefore, this assay does not account for the lower quality of islets lost (and thus not transplanted) due to fragmentation (typical of the TLM condition). Despite these limitations, persufflation as a pancreas preservation technique compared favorably against both immediate isolation and TLM in terms of diabetes reversal rates, time to diabetes reversal, and mean blood glucose (equivalent to the area under the curve) when the data from different conditions (storage time and culture time) were grouped. While the results were not statistically significant, mean blood glucose did show a trend towards statistical significance for persufflation versus immediate isolation (2-sample t test, p=0.076).

EXAMPLE 2

Additional Persufflation Experiments Using an Electrochemical Oxygen Concentrator (EOC) with Porcine and Human Pancreata These experiments included islet isolations and compared outcomes from unpreserved lobes (control) to those from lobes preserved for 24 hours with the Two Layer Method (TLM) or by persufflation. Consequently, the number of porcine pancreata used for isolation was seven, four of which were used for assessment of preservation at 6 hours and three of which were used for assessment of preservation at 24 hours. In addition to the experiments conducted with porcine pancreata, we have been able to obtain a human research-grade pancreas, which was utilized for testing the persufflation technique. Some key findings are as follows: (1) 24-hr preservation with persufflation using electrochemically generated oxygen results in superior outcomes when compared to 24-hr storage on TLM (see FIGS. 9 and 10); (2) Persufflation of the human pancreas is feasible and surgically less complex than persufflation of the porcine pancreas. In addition, persufflation of the human pancreas can be accomplished with a portion of the pancreas when the pancreas is split into 2 parts. This demonstration is important because it will enable direct and paired comparisons between persufflation-preservation and TLM or persufflation-preservation and no preservation with the same organ in future work.

In one experiment, the impact of persufflation on islet isolation was tested by dividing each porcine organ into its 3 lobes, taking the duodenal lobe for immediate isolation, preserving the splenic lobe for 24 hours with persufflation, and preserving the connecting lobe for 24 hours with TLM. The method of separating each organ into its lobes was chosen to allow paired comparison of the preservation methods by eliminating the donor variability. Because of the small sample size, it was decided to standardize (rather than randomize) the lobe used for each condition. Data from our porcine isolation database (total of ~650 isolations) indicate that there is no difference in the expected islet yield per gram of pancreatic tissue between the 3 lobes.

No noticeable differences were observed by histology between organ samples collected immediately following procurement (t=0) and those collected following 24 hours of persufflation. However, tissue preserved with TLM exhibited a high incidence of pyknotic nuclei when compared with persufflated samples, especially after 24-hour preservation, as seen in FIGS. 5(a) through 5(c).

Figure 10:
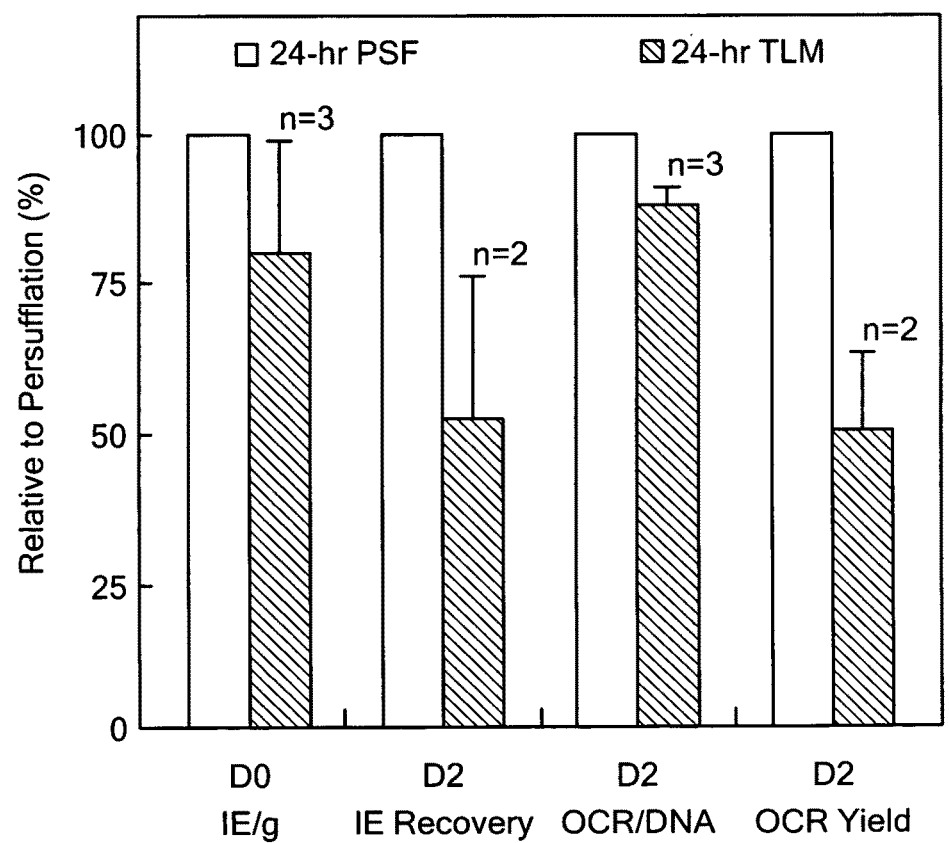
FIG. 10 is a graph, showing TLM outcomes as percentage of persufflation outcomes for the preparations discussed in Example 2 (error bars show the standard error of the mean).

FIG. 9 summarizes various measures of islet quantity and quality (averages and standard deviations) from the porcine pancreata preserved by various methods. Based on a paired two-tailed t-test, persufflation was significantly superior to TLM for Day 2 IE recovery (p=0.011, n=2) and Day 2 OCR/DNA (p=0.011, n=3). There was no statistically significant difference between immediate isolation and persufflation in any measure, even though mean values for all parameters suggested better outcomes with persufflation. FIG. 10 summarizes the TLM outcomes as a percentage of persufflation following 24-hour preservation. In addition, islets isolated from persufflated and control lobes (no storage) were implanted into diabetic athymic nude mice after culture. The TLM stored lobes did not yield sufficient islets to allow for nude mouse transplants post-culture. Early results (5 days posttransplant) indicate that 3 of the 4 mice transplanted with cultured islets obtained from lobes persufflated for 24 hours had blood sugars below 200 mg/dL (suggesting diabetes reversal), whereas only 1 of 3 mice transplanted with islets isolated from control unpreserved lobes had blood sugars below 200 mg/dL.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A method of preserving at least one organ ex vivo, said method comprising the steps of:

(a) generating in situ at least two preserving gases, wherein the at least two preserving gases comprise hydrogen gas and oxygen gas; and
(b) persufflating the at least one organ ex vivo with each of the in situ generated preserving gases.

2. The method as claimed in claim 1 wherein the at least one organ is a human organ.

3. The method as claimed in claim 2 wherein the at least one organ is a pancreas.

4. The method as claimed in claim 3 wherein the at least one organ is a human pancreas.

5. The method as claimed in claim 3 wherein the at least one organ is a porcine pancreas.

6. The method as claimed in claim 1 wherein the at least one organ is a porcine organ.

7. The method as claimed in claim 1 wherein the at least one organ is selected from the group consisting of the pancreas, the liver, the kidney, the heart, the lung, and the small intestine.

8. The method as claimed in claim 1 further comprising the step of mixing at least one of the preserving gases generated in step (a) in one or more gases to form a gas/gas mixture and wherein said persufflation step comprises persufflating the at least one organ with said gas/gas mixture.

9. The method as claimed in claim 1 wherein the at least two preserving gases further comprise gaseous carbon dioxide, gaseous carbon monoxide, and water vapor.

10. The method as claimed in claim 1 wherein said step for in situ generating the at least two preserving gases is performed electrochemically.

11. The method as claimed in claim 10 wherein said step for in situ generating the at least two preserving gases is performed using an electrolyzer.

12. The method as claimed in claim 1 wherein said step for in situ generating the oxygen gas is performed using an electrochemical oxygen concentrator.

13. The method as claimed in claim 1 wherein said step for in situ generating a preserving gas is performed by pressure swing adsorption.

14. The method as claimed in claim 1 wherein said step for in situ generating a preserving gas is performed by chemical oxygen release.

15. The method as claimed in claim 1 wherein the at least one organ is a pancreas, said method further comprising the step of mixing the in situ generated oxygen gas in ambient air to form a gas/gas mixture and wherein said persufflating step comprises persufflating the at least one organ with said gas/gas mixture.

16. The method as claimed in claim 15 wherein said gas/gas mixture has an oxygen concentration of at least approximately 20% and less than 100%.

17. The method as claimed in claim 16 wherein said gas/gas mixture has an oxygen concentration of approximately 30-80%.

18. The method as claimed in claim 17 wherein said gas/gas mixture has an oxygen concentration of approximately 40%.

19. The method as claimed in claim 15 wherein said gas/gas mixture has an oxygen concentration of approximately 40% and wherein said persufflating step comprises persufflating the at least one organ with said gas/gas mixture at a flow rate of about 15-22 cc/min and at a pressure of less than about 22 mm Hg.

20. The method as claimed in claim 19 wherein said gas/gas mixture has a temperature of about 4-8° C. at the time of persufflating the at least one organ.

21. The method as claimed in claim 1 wherein the at least one organ is a plurality of organs and wherein said persufflating step comprises persufflating the plurality of organs simultaneously.

22. The method as claimed in claim 1 further comprising the step of bathing the organ in an organ preservation solution and wherein the persufflating step is performed during said bathing step.

23. A method of pancreas preservation, said method comprising:
(a) generating in situ gaseous oxygen;
(b) mixing the in situ gaseous oxygen with ambient air to produce a preserving gas;
(c) persufflating the pancreas with the preserving gas;
(d) wherein, during said mixing step, the relative proportions of gaseous oxygen and ambient air in the preserving gas are controlled to obtain a desired oxygen concentration in the preserving gas.

24. The method as claimed in claim 23 wherein said persufflating step comprises persufflating, via cannulation, the pancreas with the preserving gas.

25. The method as claimed in claim 24 wherein the pancreas is a human pancreas.

26. The method as claimed in claim 25 wherein said persufflating step comprises persufflating the pancreas anterograde via cannulation of at least one artery.

27. The method as claimed in claim 26 wherein said cannulation comprises en bloc pancreaticoduodenectomy and/or splenectomy with division of aorta to include celiac trunk and superior mesenteric artery.

28. The method as claimed in claim 26 wherein said cannulation comprises en bloc pancreaticoduodenectomy and/or splenectomy with direct cannulation of celiac trunk and superior mesenteric artery.

29. The method as claimed in claim 26 wherein said cannulation comprises en bloc pancreaticoduodenectomy and/or splenectomy with direct cannulation of proximal splenic artery and superior mesenteric artery.

30. The method as claimed in claim 25 wherein said persufflating step comprises persufflating the pancreas retrograde via cannulation of at least one vein.

31. The method as claimed in claim 30 wherein said cannulation comprises en bloc pancreaticoduodenectomy and/or splenectomy with cannulation of inferior mesenteric vein or splenic vein.

32. The method as claimed in claim 30 wherein said cannulation comprises en bloc pancreaticoduodenectomy and/or splenectomy with cannulation of superior mesenteric vein.

33. The method as claimed in claim 30 wherein said cannulation comprises en bloc pancreaticoduodenectomy and/or splenectomy with cannulation of portal vein.

34. The method as claimed in claim 25 wherein said persufflating step comprises persufflating the human pancreas through at least one ductal entry.

35. The method as claimed in claim 25 wherein said persufflating step comprises persufflating the human pancreas both through at least one ductal entry and through at least one artery.

36. The method as claimed in claim 25 wherein said persufflating step comprises persufflating the human pancreas both through at least one ductal entry and through at least one vein.

37. The method as claimed in claim 24 wherein the pancreas is a porcine pancreas.

38. The method as claimed in claim 37 wherein said persufflating step comprises persufflating the pancreas anterograde via cannulation of at least one artery.

39. The method as claimed in claim 38 wherein said cannulation comprises en bloc pancreaticoduodenectomy and/or splenectomy with division of aorta to include celiac trunk and superior mesenteric artery.

40. The method as claimed in claim 38 wherein said cannulation comprises en bloc pancreaticoduodenectomy and/or splenectomy with direct cannulation of celiac trunk and superior mesenteric artery.

41. The method as claimed in claim 38 wherein said cannulation comprises en bloc pancreaticoduodenectomy and/or splenectomy with direct cannulation of proximal splenic artery and superior mesenteric artery.

42. The method as claimed in claim 37 wherein said persufflating step comprises persufflating the pancreas retrograde via cannulation of at least one vein.

43. The method as claimed in claim 42 wherein said cannulation comprises en bloc pancreaticoduodenectomy and/or splenectomy with cannulation of splenic vein.

44. The method as claimed in claim 43 wherein said cannulation comprises en bloc pancreaticoduodenectomy and/or splenectomy with cannulation of superior mesenteric vein.

45. The method as claimed in claim 42 wherein said cannulation comprises en bloc pancreaticoduodenectomy and/or splenectomy with cannulation of inferior mesenteric vein.

46. The method as claimed in claim 42 wherein said cannulation comprises en bloc pancreaticoduodenectomy and/or splenectomy with cannulation of portal vein.

47. The method as claimed in claim 37 wherein said persufflating step comprises persufflating the porcine pancreas through at least one ductal entry.

48. The method as claimed in claim 37 wherein said persufflating step comprises persufflating the porcine pancreas both through at least one ductal entry and through at least one artery.

49. The method as claimed in claim 37 wherein said persufflating step comprises persufflating the porcine pancreas both through at least one ductal entry and through at least one vein.

50. The method as claimed in claim 23 wherein said step for in situ generating gaseous oxygen is performed electrochemically.

51. A method of preserving at least one organ, said method comprising:
  (a) generating in situ gaseous oxygen;
  (b) mixing the gaseous oxygen with ambient air to form a preserving gas;
  (c) persufflating the at least one organ with the preserving gas;
  (d) wherein, during said mixing step, the relative proportions of gaseous oxygen and ambient air in the preserving gas are controlled to obtain a desired oxygen concentration in the preserving gas.

* * * * *

UNITED STATES PATENT AND TRADEMARK OFFICE
CERTIFICATE OF CORRECTION

PATENT NO. : 10,091,985 B2
APPLICATION NO. : 12/803083
DATED : October 9, 2018
INVENTOR(S) : Linda A. Tempelman et al.

It is certified that error appears in the above-identified patent and that said Letters Patent is hereby corrected as shown below:

In the Specification

Please replace the statement on Column 1, Lines 15-19 (provided under the Statement Regarding Federally Sponsored Research or Development) with the following replacement statement:

--This invention was made with government support under DK070400 awarded by the National Institutes of Health. The government has certain rights in the invention.--

Signed and Sealed this
Third Day of March, 2020

Andrei Iancu
*Director of the United States Patent and Trademark Office*